United States Patent [19]

Bodem et al.

[11] Patent Number: 4,481,287
[45] Date of Patent: Nov. 6, 1984

[54] 4-HYDROXYALKYL-SUBSTITUTED 3-PYRAZOLIDINONE ELECTRON TRANSFER AGENTS

[75] Inventors: George B. Bodem, Pittsford; Drake M. Michno, Webster, both of N.Y.

[73] Assignee: Eastman Kodak Company, Rochester, N.Y.

[21] Appl. No.: 590,810

[22] Filed: Mar. 19, 1984

Related U.S. Application Data

[62] Division of Ser. No. 520,086, Aug. 4, 1983.

[51] Int. Cl.³ .................. G03C 5/30; C07D 403/00; C07D 231/00
[52] U.S. Cl. ................................ 430/483; 548/364; 548/367
[58] Field of Search .............. 430/218, 440, 480, 483; 548/364, 367

[56] References Cited

U.S. PATENT DOCUMENTS

| | | | |
|---|---|---|---|
| 3,221,023 | 11/1965 | DeMarle et al. | 548/367 |
| 3,247,201 | 4/1966 | DeMarle et al. | 430/483 |
| 3,453,109 | 7/1969 | Lee | 430/440 |
| 4,076,529 | 2/1978 | Fleckenstein et al. | 430/223 |
| 4,209,580 | 6/1980 | McCreary et al. | 430/218 |

FOREIGN PATENT DOCUMENTS 54002 6/1982 European Pat. Off. .

OTHER PUBLICATIONS

Research Disclosure, vol. 161, Sep. 1977, Item 16139, p. 26.

Primary Examiner—Richard L. Schilling
Attorney, Agent, or Firm—Harold E. Cole

[57] ABSTRACT

Photographic elements, film units, processes and alkaline processing compositions are described wherein certain 4-hydroxyalkyl-substituted 3-pyrazolidinones are employed as electron transfer agents in black-and-white and color image transfer materials. The silver halide electron transfer agents or precursors thereof have the following formula:

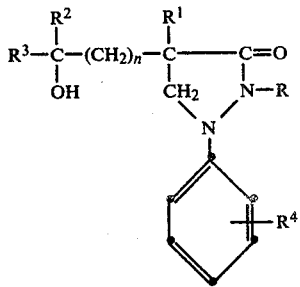

wherein:
n is 1 or 2;
R repesents hydrogen or a hydrolyzable moiety;
$R^1$ represents an alkyl or substituted alkyl group of 1 to about 6 carbon atoms, an aryl or substituted aryl group of 6 to about 10 carbon atoms, or an aralkyl group of 6 to about 10 carbon atoms;
$R^2$ and $R^3$ each independently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms; and
$R^4$ represents hydrogen or one or more alkyl or alkoxy groups having from 1 to about 4 carbon atoms, methylenedioxy groups or ethylenedioxy groups.

9 Claims, No Drawings

4-HYDROXYALKYL-SUBSTITUTED 3-PYRAZOLIDINONE ELECTRON TRANSFER AGENTS

This is a division of application Ser. No. 520,086, filed Aug. 4, 1983.

This invention relates to photography, and more particularly to black-and-white and color diffusion transfer photography wherein certain novel 4-hydroxyalkyl-substituted 3-pyrazolidinones are used as electron transfer agents. Post-processing $D_{min}$ stability is thereby greatly improved in accordance with this invention.

Various formats for color, integral transfer elements are described in the prior art, such as U.S. Pat. Nos. 3,415,644; 3,415,645; 3,415,646; 3,647,437; 3,635,707; 3,756,815, and Canadian Pat. Nos. 928,559 and 674,082. In these formats, the image-receiving layer containing the photographic image for viewing remains permanently attached and integral with the image generating and ancillary layers present in the structure when a transparent support is employed on the viewing side of the assemblage. The image is formed by dyes, produced in the image generating units, diffusing through the layers of the structure to the dye image-receiving layer. After exposure of the assemblage, an alkaline processing composition permeates the various layers to initiate development of the exposed photosensitive silver halide emulsion layers. The emulsion layers are developed in proportion to the extend of the respective exposures, and the image dyes which are formed or released in the respective image generating layers begin to diffuse throughout the structure. At least a portion of the imagewise distribution of diffusible dyes diffuse to the dye image-receiving layer to form an image of the original subject.

Other so-called "peel apart" formats for color diffusion transfer assemblages are described, for example, in U.S. Pat. Nos. 2,983,606; 3,362,819 and 3,362,821. In these formats, the image-receiving element is separated from the photosensitive element after development and transfer of the dyes to the image-receiving layer has occurred.

U.S. Pat. Nos. 4,076,529 of Fleckenstein et al, issued Feb. 28, 1978, describes various color image transfer elements which employ nondiffusible, redox dye-releasing (RDR) compounds which are alkali-cleavable upon oxidation to release a diffusible color-providing moiety. An electron transfer agent (ETA) is oxidized as a function of development. The $ETA_{ox}$ then cross-oxidizes the RDR. The ETA compounds described therein include various pyrazolidinones, such as 1-phenyl-3-pyrazolidinone, 1-phenyl-4,4-dimethyl-3-pyrazolidinone and 4-hydroxymethyl-4-methyl-1-phenyl-3-pyrazolidinone.

Two important consideration for a practical image transfer system are to provide an ETA with low stain and high activity. While 4,4-dialkyl-1-phenyl-3-pyrazolidinones have these dual advantages, there is a problem in that they release nitrogen gas upon oxidation. In areas of silver development, reduction of silver halide to metallic silver is accompanied by gas evolution. This gas causes image degradation by minute lower dye density spots in high dye density areas. This is probably due to the gas bubbles forming barriers to migrating imaging dye.

U.S. Pat. No. 4,209,580 of McCreary et al relates to 1-phenyl-3-pyrazolidinone ETAs having a 4-hydroxymethyl group. Upon oxidation, these compounds are believed to undergo a retro-Prin's reaction (See *Advanced Organic Chemistry*, J. March, 2nd Ed., 1977, MrGraw-Hill Book Co.), which is characteristic of β-hydroxy ketones, to yield a relatively stable species that does not evolve nitrogen. However, as will be shown by comparative tests hereinafter, the compounds of this invention provide low $D_{mins}$ and higher $D_{maxes}$ than the closely related compounds of this patent.

U.S. Pat. Nos. 3,221,023, 3,247,201 and 3,453,109 European Pat. No. 54,002 and *Research Disclosure*, Vol. 161, September 1977, item 16139, page 26, relate to various 4-hydroxyalkyl substituents on 3-pyrazolidinones. However, the compounds of this invention are not specifically taught by these references. As will be shown by comparative tests hereinafter, the compounds of this invention have unexpected advantages over the closely related homologues disclosed in the prior art.

It would be desirable to provide improved ETA's that have good image discrimination, relatively low stain, lower $D_{min}$'s, minimal nitrogen evolution upon oxidation and good stability in highly alkaline processing compositions (i.e., do not crystallize from or decompose in these compositions) over those of the prior art.

These and other advantages are provided by the 4-hydroxyalkyl-substituted 3-pyrazolidinone compounds of this invention which are silver halide ETA's or precursors thereof and which have the following formula:

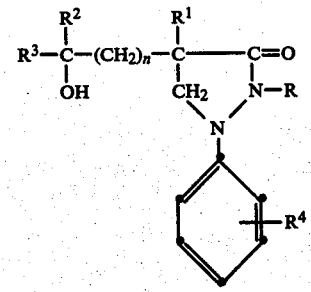

wherein:

n is 1 or 2;

R represents hydrogen or a hydrolyzable moiety;

$R^1$ represents an alkyl or substituted alkyl group of 1 to about 6 carbon atoms such as methyl, ethyl, propyl, sec-butyl, hydroxyethyl, ethoxy, methoxy, N,N-dimethylaminoethyl or allyl; an aryl or substituted aryl group of 6 to about 10 carbon atoms such as phenyl, p-tolyl, 2,4-xylyl, p-methoxyphenyl, p-carbonamidophenyl or p-hydroxymethylphenyl; or an aralkyl group of 6 to about 10 carbon atoms such as benzyl or phenethyl;

$R^2$ and $R^3$ each independently represents hydrogen, an alkyl or substituted alkyl group of 1 to about 6 carbon atoms such as methyl ethyl, propyl, sec,-butyl, hydroxyethyl, ethoxy, methoxy, N,N-dimethylaminoethyl or allyl; an aryl or substituted aryl group of 6 to about 10 carbon atoms such as phenyl, p-tolyl, 2,4-xylyl, p-methoxyphenyl, p-carbonamidophenyl or p-hydroxymethylphenyl; or an aralkyl group of 6 to about 10 cabon atoms such as benzyl or phenethyl; and $R^4$ represents hydrogen or one or more alkyl or alkoxy groups having from 1 to about 4 carbon atoms, such as methyl, ethyl, butyl, methoxy, ethoxy or propoxy; methylenedioxy groups or ethylenedioxy groups.

R in the above formula can be hydrogen or any hydrolyzable moiety well known to those skilled in the art, such as acetyl, mono-, di- or trichloroacetyl radicals, perfluoroacyl, pyruvyl, alkoxyacyl, nitrobenzoyl, cyanobenzoyl, sulfonyl, sulfinyl, or a blocking group as disclosed in Mooberry and Archie U.S. Pat. No. 4,358,525.

When R in the above formula is hydrogen, the compound formula may be written in the keto form as:

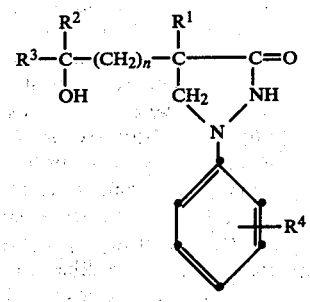

or in the enol form as:

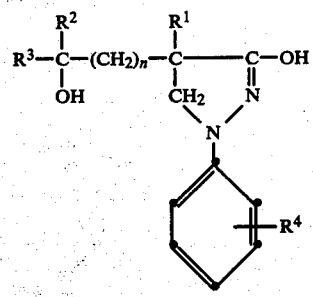

As used herein, the keto form is meant to include the enol form and vice versa.

When R is in the above formula is a hydrolyzable moiety, then the compound is an ETA precursor and can be incorporated into a photographic element, cover sheet, receiving element etc. Such compounds would be represented by the same general formula as above, except that "R" would be "$R^5$", wherein $R^5$ is a hydrolyzable moiety. During the processing of a photographic element containing an ETA precursor, $R^5$ will become hydrolyzed by the alkaline processing composition to become hydrogen. When used in this manner, the ETA precursor can be employed in any concentration effective for the intended purpose. Good results have been obtained when the ETA precursor is employed at a concentration of from about 0.05 to 2.0 mmoles/m² of element, preferably 0.1 to 1.5 mmoles/m².

ETA's directly incorporated into an alkaline processing composition will be subject to hydrolysis, so that R in the above formula intrinsically represents hydrogen. When employed in an alkaline processing composition, good results have been obtained when the ETA is present at a concentration of from about 0.1 to about 30 grams per liter, and preferably from about 2 to about 15 grams per liter.

In a preferred embodiment of this invention, $R^1$ is methyl and $R^2$ and $R^3$ hydrogen. In another preferred embodiment of this invention, $R^1$ is methyl, $R^2$ is hydrogen, n is 1 and $R^3$ is methyl or ethyl. In yet another preferred embodiment of this invention, $R^4$ is methyl or methoxy located in the para-position.

In addition to $R^4$, the phenyl ring in the above formula may also be substituted with any substituent as long as the photographic activity of the ETA is not impaired. Such other substituents include, for example, chloro, benzyl, dialkylamino or alkoxycarbonyl.

The compounds of this invention can undergo a four-electron oxidation with a strong oxidant which is accompanied by the formation of a new absorption spectrum. No retro-Prins reaction is possible because these materials are not β-hydroxy olefins. It is believed that the compounds of this invention ring close to form a new, relatively stable species as shown by the following illustration with a preferred embodiment:

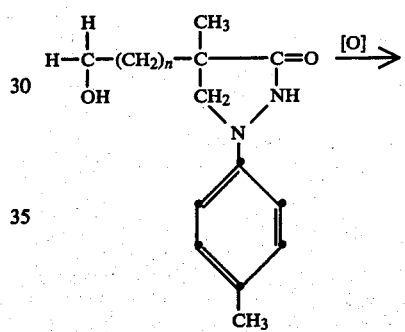

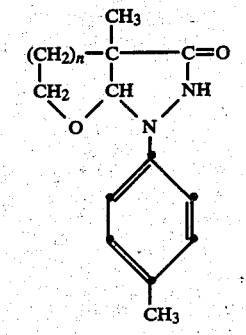

A 5- or 6-membered ring is formed, depending upon whether n is 1 or 2. A similar attempt at ring closure of the corresponding 4-hydroxymethyl compound would involve a highly unlikely 4-membered ring. Thus, it is believed that the ring closure which our compounds undergo to form a relatively stable species does not evolve nitrogen, while corresponding 4-hydroxymethyl compounds, which cannot ring close, do release nitrogen upon oxidation, as discussed above.

Examples of compounds useful as an ETA or precursor thereof in accordance with this invention have the following formulae:

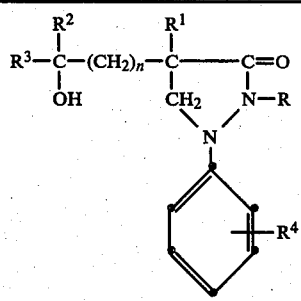

| Cmpd. No. | R | R¹ | R² | R³ | R⁴ | n |
| --- | --- | --- | --- | --- | --- | --- |
| 1 | H | $CH_3$ | H | H | 4'-$CH_3$ | 1 |
| 2 | H | $CH_3$ | H | H | 4'-$CH_3$ | 2 |
| 3 | H | $CH_3$ | $CH_3$ | H | 4'-$CH_3$ | 1 |
| 4 | H | $CH_3$ | $C_2H_3$ | H | 4'-$CH_3$ | 1 |
| 5 | H | $CH_3$ | H | H | 4'-$CH_3$ | 1 |
| 6 | H | $OCH_3$ | H | H | 4'-$OCH_3$ | 1 |
| 7 | H | $CH_2CH=CH_2$ | H | H | 4'-$CH_3$ | 1 |
| 8 | H | $CH_2CH_2OH$ | H | H | 4'-$OCH_3$ | 1 |
| 9 | H | $CH_2C_6H_5$ | H | H | 3',4'-$OCH_2O-$ | 1 |
| 10 | H | $CH_3$ | $CH_3$ | H | 3',4'-$OCH_2O-$ | 2 |
| 11 | H | $C_3H_7$ | H | H | 4'-$OCH_3$ | 1 |
| 12 | H | p-$C_6H_4OCH_3$ | H | H | 4'-$OCH_3$ | 1 |
| 13 | H | p-$CH_2C_6H_4OH$ | H | H | 4'-$CH_3$ | 1 |
| 14 | $CO_2C_4H_9$ | $CH_3$ | $C_2H_5$ | $CH_3$ | 4'-$C_3H_7$ | 2 |
| 15 | $COCH_3$ | $CH_3$ | H | H | 3',4'-$OCH_2O-$ | 1 |
| 16 | $CO_2CH_2C_6H_5$ | $CH_3$ | H | H | 4'-$OC_2H_5$ | 1 |
| 17 | $COCH_2C_6H_5$ | $C_2H_5$ | H | H | 4'-$C_4H_9$ | 1 |
| 18 | $CON(CH_3)C_6H_4-$ o-$COCH_2Cl$ | $CH_3$ | H | H | 4'-$OCH_3$ | 1 |
| 19 | H | $CH_2CH_2N(CH_3)_2$ | H | H | 4'-$C_4H_9$ | 2 |
| 20 | $CON(CH_3)C_6H_4-$ o-$CH_2N(CH_3)COCF_3$ | $CH_3$ | H | H | 4'-$OCH_3$ | 1 |
| 21 | H | $CONHC_6H_5$ | H | H | 3',4'-$OCH_2CH_2O-$ | 2 |
| 22 | H | ![2,5-dimethylfuran]$CH_3$ / $CH_3$ | H | H | 3',4'-$OC_2H_5$ | 1 |
| 23 | H | $CH_3$ | $CH_3$ | H | 3',4'-$OCH_3$ | 1 |
| 24 | H | $CH_3$ | $CH_3$ | $CH_3$ | 3',4'-$CH_3$ | 1 |

The ETA's described herein can be prepared by reaction of a substituted hydrazine with a β-halogenated or β-hydroxy acid chloride or carboxylic acid as shown in U.S. Pat. No. 2,289,367 and EP No. 55,900, the disclosures of which are hereby incorporated by reference. Another synthetic procedure involves transient blockings with a trialkylsilyl group, addition of the desired electrophile in the presence of a strong base, followed by removal of the blocking group by hydrolysis. This is described and claimed in Michno U.S. application Ser. No. 520,085, filed of even date herewith, entitled PREPARATION OF 4-SUBSTITUTED 3-PYRAZOLIDINONES, the disclosure of which is hereby incorporated by reference.

A photographic element according to this invention comprises a support having thereon at least one photosensitive silver halide emulsion layer having associated therewith a dye image-providing material, and containing an ETA precursor according to the formula above where R is a hydrolyzable moiety.

A dye image-receiving element according to this invention comprises a support having thereon a dye image-receiving layer and containing an ETA precursor according to the formula above where R is a hydrolyzable moiety.

A process for producing a photographic image in color according to this invention comprises:

treating an imagewise-exposed photographic element, comprising a support having thereon at least one photosensitive silver halide emulsion layer having associated therewith a dye image-providing material, with an alkaline processing composition in the presence of a silver halide ETA to effect development of each exposed silver halide emulsion layer, whereby:
 (a) an imagewise distribution of dye is formed as a function of the development of the silver halide emulsion layer; and
 (b) at least a portion of the imagewise distribution of the dye diffuses out of the element, such as to a dye image-receiving layer.

In the above process, the ETA may be located in the alkaline processing composition or may be located in the photographic element (or in a cover sheet or receiving element) in its "blocked" precursor form.

It will be appreciated that, after processing the photographic element described above, there remains in the element, after transfer has taken place, an imagewise distribution of dye in addition to developed silver. A color image comprising residual nondiffusible compound may be obtained in this element if the residual silver and silver halide are removed in any conventional manner well known to those skilled in the photographic art, such as a bleach bath followed by a fix bath, a bleach-fix bath, etc. The imagewise distribution of dye may also diffuse out of this element into these baths, if desired, rather than to an image-receiving element.

The photographic element in the above-described process can be treated with an alkaline processing composition to effect or initiate development in any manner. A preferred method for applying processing composition is by use of a rupturable container or pod which contains the composition. The processing composition employed in this invention can contain the ETA for development, although the composition could also be solely an alkaline solution where the ETA is incorporated in the photographic element, the image-receiving element or the cover sheet. In these instances, the alkaline solution serves to activate the incorporated ETA.

A photographic assemblage or film unit in accordance with this invention is adapted to be processed by an alkaline processing composition, and comprises:

(1) a photographic element comprising a support having thereon at least one photosensitive silver halide emulsion layer having associated therewith a dye image-providing material; and
(2) a dye image-receiving layer, the assemblage containing the ETA or precursor thereof as described above. In this embodiment, the processing composition may be inserted into the film unit such as by interjecting processing solution with communicating members similar to hypodermic syringes which are attached either to a camera or camera cartridge. The processing composition may also be applied by means of a swab or by dipping in a bath, if so desired. In a preferred embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit. As previously described, the ETA can be located in the assemblage in the processing composition. Alternatively, an ETA precursor can be located in the photographic element or in an image-receiving element, cover sheet or process sheet, as described previously.

The dye image-providing material useful in this invention is either positive- or negative-working, and is either initially mobile or immobile in the photographic element during processing with an alkaline composition. Examples of initially mobile, positive-working dye image-providing materials useful in this invention are described in U.S. Pat. Nos. 2,983,606; 3,536,739; 3,705,184; 3,482,972; 2,756,142; 3,880,658 and 3,854,985. Examples of negative-working dye image-providing materials useful in this invention include conventional couplers which react with oxidized aromatic primary amino color developing agents to produce or release a dye such as those described, for example, in U.S. Pat. No. 3,227,550 and Canadian Pat. No. 602,607. In a preferred embodiment of this invention, the dye image-providing material is a ballasted, redox-dye-releasing (RDR) compound. Such compounds are well known to those skilled in the art and are, generally speaking, compounds which will react with oxidized or unoxidized developing agent or electron transfer agent to release a dye. Such nondiffusible RDRs include negative-working compounds, as described in U.S. Pat. Nos. 3,728,113 of Becker et al; 3,725,062 of Anderson and Lum; 3,698,897 of Gompf and Lum; 3,628,952 of Puschel et al; 3,443,939 and 3,443,940 of Bloom et al; 4,053,312 of Fleckenstein; 4,076,529 of Fleckenstein et al; 4,055,428 of Koyama et al; 4,149,892 of Deguchi et al; 4,198,235 and 4,179,291 of Vetter et al; *Research Disclosure* 15157, Nov., 1976 and *Research Disclosure* 15654, Apr. 1977. Such nondiffusible RDR's also include positive-working compounds, as described in U.S. Pat. Nos. 3,980,479; 4,139,379; 4,139,389; 4,199,354, 4,232,107, 4,199,355 and German Pat. No. 2,854,946, the disclosures of which are hereby incorporated by reference.

In a preferred embodiment of the invention, RDR's such as those in the Fleckenstein et al patent referred to above are employed. Such compounds are ballasted sulfonamido compounds which are alkali-cleavable upon oxidation to release a diffusible dye from the nucleus and have the formula:

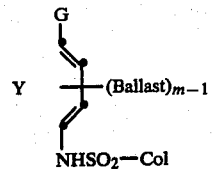

wherein:
(a) Col is a dye or dye precursor moiety;
(b) Ballast is an organic ballasting radical of such molecular size and configuration (e.g., simple organic groups or polymeric groups) as to render the compound nondiffusible in the photosensitive element during development in an alkaline processing composition;
(c) G is $OR^6$ or $NHR^7$ wherein $R^6$ is hydrogen or a hydrolyzable moiety and $R^7$ hydrogen or a substituted or unsubstituted alkyl group of 1 to 22 carbon atoms, such as methyl, ethyl, hydroxyethyl, propyl, butyl, secondary butyl, tertiary butyl, cyclopropyl, 4-chlorobutyl, cyclobutyl, 4-nitroamyl, hexyl, cyclohexyl, octyl, decyl, octadecyl, docosyl, benzyl or phenethyl (when $R^7$ is an alkyl group of greater than 6 carbon atoms, it can serve as a partial or sole Ballast group);
(d) Y represents the atoms necessary to complete a benzene nucleus, a naphthalene nucleus or a 5- to 7-membered heterocyclic ring such as pyrazolone or pyrimidine; and
(e) m is a positive integer or 1 or 2 and is 2 when G is $OR^6$ or when $R^7$ is a hydrogen or an alkyl group of less than 8 carbon atoms.

For further details concerning the above-described sulfonamido compounds and specific examples of same, reference is made to the above-mentioned Fleckenstein et al U.S. Pat. No. 4,076,529.

In another preferred embodiment of the invention, positive-working, nondiffusible RDR's of the type disclosed in U.S. Pat. Nos. 4,139,379 and 4,139,389 are employed. In this embodiment, an immobile compound is employed which as incorporated in a photographic element is incapable of releasing a diffusible dye. However, during photographic processing under alkaline conditions, the compound is capable of accepting at least one electron (i.e., being reduced) and thereafter releases a diffusible dye. These immobile compounds are ballasted electron accepting nucleophilic displacement compounds.

In this invention, dye image-providing materials can be used which produce diffusible dye images as a function of development. Either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained on the dye image-receiving layer by using ballasted, redox dye-releasers. After exposure of the film unit, the alkaline processing composition permeates the various layers to initiate development of the exposed photosensitive silver halide emulsion layers. The ETA present in the film unit develops each of the silver halide emulsion layers in the unexposed areas (since the silver halide emulsions are direct-positive ones), thus causing the ETA to become oxidized imagewise corresponding to the unexposed areas of the direct-positive silver halide emulsion layers. The oxidized ETA then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Reseach Disclosure*, pages 76 through 79, the disclosure of which is hereby incorporated by reference.

The dye image-receiving layer in the above-described film assemblage is optionally located on a separate support adapted to be superposed on the photographic element after exposure thereof. Such image-receiving elements are generally disclosed, for example, in U.S. Pat. No. 3,362,819. In accordance with this embodiment of the invention, the dye image-receiving element would comprise a support having thereon, in sequence, a neutralizing layer, a timing layer and a dye image-receiving layer. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

In another embodiment, the dye image-receiving layer in the above-described film assemblage is located integral with the photographic element and is located between the support and the lowermost photosensitive silver halide emulsion layer. one useful format for integral imaging receiver photographic elements is disclosed in Belgian Pat. No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgain Pat. No. 757,960.

Another format for integral imaging receiver photographic elements in which the present invention is employed is disclosed in Canadian Pat. No. 928,559. In this embodiment, the support for the photographic element is transparent and is coated with the image-receiving layer, a substantially opaque, light-reflective layer and the photosensitive layer or layers described above. A rupturable container, containing an alkaline processing composition including an ETA and an opacifier, is positioned between the top layer and a transparent cover sheet which has thereon, in sequence, a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images, formed as a result of development, diffuse to the image-receiving layer to provide, right-reading image which is viewed through the transparent support on the opaque reflecting layer background. For further details concerning the format of this particular integral film unit, reference is made to the above-mentioned Canadian Pat. No. 928,559.

Still other useful integral formats in which this invention can be employed are described in U.S. Pat Nos. 3,415,644; 3,415,645; 3,415,646; 3,647,437 and 3,635,707. In most of these formats, a photosensitive silver halide emulsion is coated on an opaque support and a dye image-receiving layer is located on a separate transparent support superposed over the layer outermost from the opaque support. In addition, this transparent support also contains a neutralizing layer and a timing layer underneath the dye image-receiving layer.

In another embodiment of the invention, the neutralizing layer and timing layer are located underneath the photosensitive layer or layers. In that embodiment, the photographic element would comprise a support having thereon, in sequence, a neutralizing layer, a timing layer and at least one photosensitive silver halide emulsion layer having associated therewith a dye image-providing material. A dye image-receiving layer would be provided on a second support with the processing composition being applied therebetween. This format could either be peel-apart or integral, as described above.

The film unit or assemblage of the present invention is used to produce positive images in single or multicolors. In a three-color system, each silver halide emulsion layer of the film assembly will have associated therewith a dye image-providing material which releases a dye possessing a predominant spectral absorption within the region of the visible spectrum to which said silver halide emulsion is sensitive, i.e., the blue-sensitive silver halide emulsion layer will have a yellow dye image-providing material associated therewith, the green-sensitive silver halide emulsion layer will have a magenta dye image-providing material associated therewith and the red-sensitive silver halide emulsion layer will have a cyan dye image-providing material associated therewith. The dye image-providing material associated with each silver halide emulsion layer is contained either in the silver halide emulsion layer itself or in a lyer contiguous to the silver halide emulsion layer, i.e., the dye image-providing material can be coated in a separate layer underneath the silver halide emulsion layer with respect to the exposure direction.

The concentration of the dye image-providing material that is employed in the present invention can be varied over a wide range, depending upon the particular compound employed and the results desired. For example, a dye image-providing material coated in a layer at a concentration of 0.1 to 3 g/m$^2$ has been found to be useful. The dye image-providing material can be dispersed in a hydrophilic film-forming natural material or synthetic polymer, such as gelatin, polyvinyl alcohol, etc, which is adapted to be permeated by aqueous alkaline processing composition.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye later or a yellow colloidal silver layer can be present between the blue-sensitive and green-sensitive silver halide emulsion layers for absorbing or filtering blue radiation that is transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention is disclosed in U.S. Pat. Nos. 2,543,181; 2,643,886; 2,653,732; 2,723,051; 3,056,492; 3,056,491 and 3,152,515. In general, such containers comprise a rectangular sheet of fluid-and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed together with the dye image-providing material in gelatin or another aqueous alkaline solution-permeable polymeric binder and are about 0.6 to 7 microns in thickness; and the alkaline solution-permeable polymeric interlayers, e.g., gelatin, are about 0.2 to 5 microns in thickness. Of course, these thicknesses are approximate only and can be modified according to the product desired. The silver halide emulsions and dye releases may also be coated in separate layers, if desired.

Scavengers for oxidized developing agents can be employed in various interlayers of the photographic elements of the invention. Suitable materials are disclosed on page 83 of the November 1976 edition of *Research Disclosure*, the disclosure of which is hereby incorporated by reference.

Any material is useful as the image-receiving layer in this invention, as long as the desired function of mordanting or otherwise fixing the dye images is obtained. The particular material chosen will, of course, depend upon the dye to be mordanted. Suitable materials are disclosed on pages 80 through 82 of the November, 1976 edition of *Research Disclosure*, the disclosure of which is hereby incorporated by reference.

Use of a neutralizing material in the film assemblages of this invention will usually increase the stability of the transferred image. Generally, the neutralizing material will effect a reduction in the pH of the image from about 13 or 14 to at least 11 and preferably 5 to 8 within a short time after treatment with alkali. Suitable materials and their functioning are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the neutralizing layer which "times" or controls the pH reduction as a function of the rate at which alkali diffuses through the inert spacer layer. Examples of such timing layers and their functioning are disclosed in the *Research Disclosure* articles mentioned in the paragraph above concerning neutralizing layers.

The alkaline processing composition employed in this invention is the conventional aqueous solution of an alkaline material, e.g, alkali metal hydroxides or carbonates such as sodium hydroxide, sodium carbonate or an amine such as diethylamine, preferably possessing a pH in excess of 11 and preferably containing an ETA as described previously. Suitable materials and addenda frequently added to such compositions are disclosed on pages 79 and 80 of the November, 1976 edition of *Research Disclosure*, the disclosure of which is hereby incorporated by reference.

The alkaline solution permeable, substantially opaque, light-reflective layer employed in certain embodiments of photographic film units used in this invention is described more fully in the November, 1976 edition of *Research Disclosure*, page 82, disclosure of which is hereby incorporated by reference.

The supports for the photographic elements used in this invention can be any material, as long as it does not deleteriously affect the photographic properties of the film unit and is dimensionally stable. Typical flexible sheet materials are described on page 85 of the November, 1976 edition of *Research Disclosure*, the disclosure of which is hereby incorporated by reference.

While the invention has been described with reference to layers of silver halide emulsions and dye image-providing materials, dotwise coating, such as would be obtained using gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone. In an alternative embodiment, the emulsions sensitive to each of three primary regions of the spectrum can be disposed as a single segmented layer, e.g., as by the use of microvessels as described in Whitmore U.S. Pat. No. 4,362,806, issued Dec. 7, 1982.

The silver halide emulsions useful in this invention, both negative-working and direct-positive ones, are well known to those skilled in the art and are described in *Research Disclosure,* Volume 176, December, 1978, Item 17643, pages 22 and 23, "Emulsion preparation and types"; they are usually chemically and spectrally sensitized as described on page 23, "Chemical sensitization", and "Spectral sensitization and desensitization", of the above article; they are optionally protected against the production of fog and stabilized against loss of sensitivity during keeping by employing the materials described on pages 24 and 25, "Antifoggants and stabilizers", of the above article; they usually contain hardeners and coating aids as described on page 26, "Hardeners", and pages 26 and 27, "Coating aids", of the above article; they and other layers in the photographic elements used in this invention usually contain plasticizers, vehicles and filter dyes described on page 27, "Plasticizers and lubricants"; page 26, "Vehicles and vehicle extenders"; and pages 25 and 26, "Absorbing and scattering materials", of the above article; they and other layers in the photographic elements used in this invention can contain addenda which are incorporated by using the procedures described on page 27, "Methods of addition", of the above article; and they are usually coated and dried by using the various techniques described on pages 27 and 28, "Coating and drying procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein as intended to mean that the materials can be in either the same or different layers, so long as the materials are accessible to one another.

The following examples are provided to further illustrate the invention.

EXAMPLE 1

A cover sheet was prepared by coating the following layers, in the order recited, on a poly(ethylene terephthalate) film support:
(1) an acid layer comprising poly(n-butyl acrylate-co-acrylic acid), (30:70 weight ratio equivalent to 140 meq. acid/m$^2$); and
(2) a timing layer comprising 5.4 g/m$^2$ of a 1:1 physical mixture by weight of poly(acrylonitrile- co-vinylidene chloride-co-acrylic acid latex) (weight ratio of 14/80/6) and a carboxy ester lactone formed by cyclization of a vinyl acetate-maleic anhydride copolymer in the presence of 1-butanol to produce a partial butyl ester, ratio of acid:ester of 15:85. This layer also contained 0.22 g/m$^2$ of t-butylhydroquinone monoacetate and 0.16 g/m$^2$ of 1-phenyl-5-phthalimidomethyl-thiotetrazole.

An integral imaging-receiver (IIR) element was prepared by coating the following layers in the order recited on a transparent poly(ethylene terephthalate) film support. Quantities are parenthetically given in grams per square meter, unless otherwise stated.
(1) image- receiving layer of poly(styrene-co-1-vinylimidazole-co-3-benzyl-1-vinylimidazolium chloride) (50:40:10 motor ratio) (2.4), poly- (styrene-co-N-benzyl-N,N-dimethyl-N-vinylbenzyl ammonium chloride-co-divinylbenzene (molar ratio 49/49/2) (1.3) and gelatin (3.8);
(2) reflecting layer of titanium dioxide (17.0) and gelatin (2.6);
(3) opaque layer of carbon black (1.0) and gelatin (0.81);
(4) stripping layer of hydroxyethyl cellulose (0.81);
(5) interlayer of gelatin (0.54);
(6) cyan dye-providing layer of gelatin (0.54) and cyan RDR A (0.38);
(7) interlayer of cyan RDR A (0.054) and gelatin (0.54);
(8) red-sensitive, direct-positive silver bromide emulsion (0.91 silver), gelatin (0.91), Nucleating Agent B (29 mg/Ag mole), Nucleating Agent C (1.4 mg/Ag mole), titanium dioxide (0.81) and 2-(2-octadecyl)-5-sulfohydroquinone potassium salt (0.17);
(9) interlayer of gelatin (1.2) and 2,5-di-sec-dodecylhydroquinone (1.1);
(10) magenta dye-providing layer of magenta RDR B (0.43) and gelatin (0.86);
(11) interlayer of gelatin (0.81);
(12) green-sensitive, direct-positive silver bromide emulsion (0.91 silver), gelatin (0.91), Nucleating Agent A (1.9 mg/Ag mole), Nucleating Agent B (20 mg/Ag mole), titanium dioxide (0.22) and 2-(2-octadecyl)-5-sulfohydroquinone potassium salt (0.043 mg/Ag mole);
(13) interlayer of green-sensitive negative silver bromide emulsion (0.08 Ag), 2,5-di-sec-dodecylhydroquinone (1.2) and gelatin (1.3);
(14) yellow dye-providing layer of yellow RDR C (0.32); yellow RDR D (0.22), hardener bis(vinylsulfonyl) methane at 0.67% of the total gelatin weight, zinc oxide (0.11) and gelatin (1.2);
(15) blue-sensitive, direct-positive silver bromide emulsion (0.91 silver), gelatin (0.91), Nucleating Agent A (1.1 mg/Ag mole), Nucleating Agent B (76.0 mg/Ag mole), 2-(2-octadecyl)-5-sulfohydroquinone potassium salt (0.043), t-butylhydroquinone monoacetate (0.016) and titanium dioxide (0.27 ); and
(16) overcoat layer of 2,5-di-sec-dodecylhydroquinone (0.11) and gelatin (0.89).

The direct-positive emulsions are approximately 1.25μ monodispersed, octahedral, internal image silver bromide emulsions, as described in U.S. Pat. No. 3,923,513.

Cyan RDR A

-continued

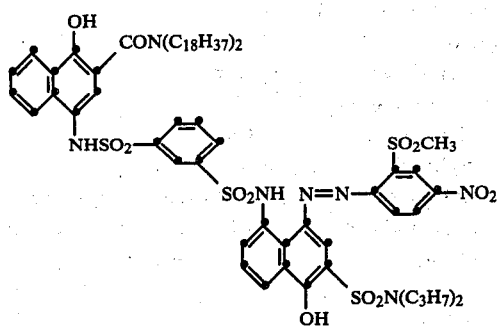

(Dispersed in N—n-butylacetanilide) (RDR/solvent ratio 1:2).

Magenta RDR B

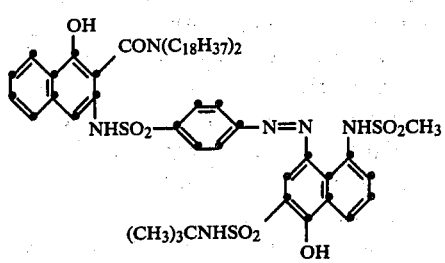

(Dispersed in diethyllauramide) RDR/solvent ratio 1:2).

Yellow RDR C

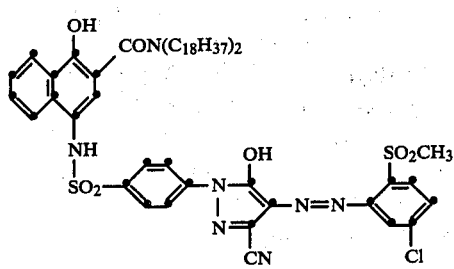

(Dispersed in diethyllauramide) (RDR/solvent ratio 1:2).

Yellow RDR D

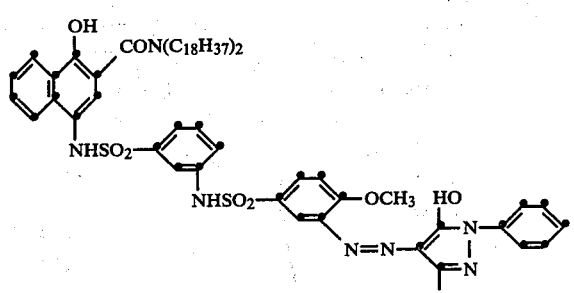

(Dispersed in di-n-butyl phthalate) (RDR/solvent ratio 1:2)

Nucleating Agent A

Nucleating Agent B

-continued

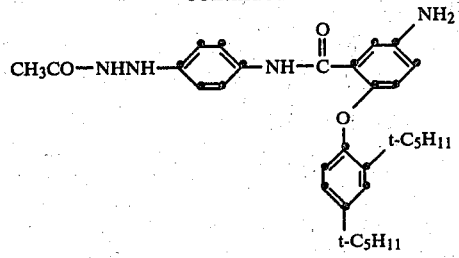

Nucleating Agent C

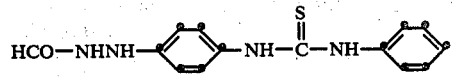

Pods containing the following processing composition were prepared.

|  | Pod Composition |
|---|---|
| Potassium hydroxide | 52.2 g |
| 5-Methylbenzotriazole | 4.0 g |
| Carboxymethylcellulose | 46 g |
| Potassium fluoride | 10 g |
| Tamol SN ® dispersant | 6.4 g |
| Potassium sulfite (anhydrous) | 1.0 g |
| 1,4-cyclohexanedimethanol | 3.0 g |
| ETA (as specified in Table 1) | 0.059 M |
| Water to 1 liter. | |

Samples of the IIR were exposed in a sensitometer through a graduated-density test object to yield a full-scale $D_{max}$–$D_{min}$ image after processing with the above viscous processing composition in a pod. The processing composition was spread at room temperature between IIR and the cover sheet described above by using a pair of juxtaposed rollers at a gap of 100 μ. Within 3 hours, the Status A density of the receiver side of the IIR was read to obtain the sensitometric parameters. The quantity of nitrogen gas evolved in a no-exposure area (maximum silver development) was determined by counting the number of bubble defects in a defined area (52 mm²) using a 10X magnification microscope.

The following results were obtained:

TABLE 1

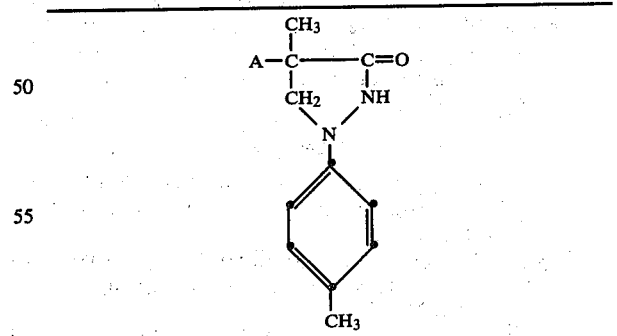

| ETA in Pod | A | Number of Bubbles (52 mm² area) | $D_{max}/D_{min}$ | | |
|---|---|---|---|---|---|
| | | | R | G | B |
| Control 1 | —CH₃ | 254 | 1.4/ 0.19 | 1.4/ 0.17 | 1.3/ 0.18 |
| Control 2 | —CH₂OH | 11 | 1.8/ 0.20 | 1.8/ 0.21 | 1.9/ 0.23 |
| Compound 1 | —(CH₂)₂OH | 23 | 2.1/ | 1.9/ | 1.6/ |

TABLE 1-continued

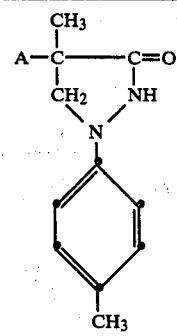

| ETA in Pod | A | Number of Bubbles (52 mm² area) | $D_{max}/D_{min}$ | | |
|---|---|---|---|---|---|
| | | | R | G | B |
| Compound 2 | —(CH₂)₃OH | 19 | 0.19 / 2.0/ 0.19 | 0.17 / 1.9/ 0.17 | 0.19 / 1.9/ 0.20 |

The above results indicate that the compounds of the invention evolved less than 10% of the nitrogen (via bubble count) compared to Control 1, and gave better image descrimination (higher $D_{max}$ with no increase in $D_{min}$. Control Compound 2 evolved little nitrogen, but had higher $D_{min}$ and lower red and green $D_{maxes}$ than the compounds of the invention.

EXAMPLE 2

An image-receiving element without any silver halide was prepared by coating the following layers in the order recited on a transparent poly(ethylene terephthalate) film support. Quantities are parenthetically given in grams per square meter.

(1) image-receiving layer of poly(styrene-co-1-vinylimidazole-co-3-benzyl-1-vinylimidazolium chloride) (50:40:10 molar ratio) (4.8) and gelatin (2.2);
(2) reflecting layer of titanium dioxide (17.0), formaldehyde (0.006) and gelatin (2.7);
(3) opaque layer of carbon black (1.9) and gelatin (1.2);
(4) interlayer of gelatin (0.54);
(5) stripping layer of hydroxyethyl cellulose (0.81); and
(6) overcoat layer of hardener bis(vinylsulfonyl)- methane (0.01) and gelatin (1.1).

The same type of pod and cover sheet were used as in Example 1, using the ETA's in the processing composition as identified in Table 2.

The processing composition was spread between the IIR and cover sheet using a pair of 100 μ gap juxtaposed rollers. One hour after lamination, the cover sheet was peeled from the IIR and discarded. The separated IIR was incubated for 4 weeks at 32° C./15% RH. The stain of this "$D_{min}$ area" was evaluated by recording the spectrum using a scanning spectrophotometer. The μmax of the stain and its density were measured as follows:

TABLE 2

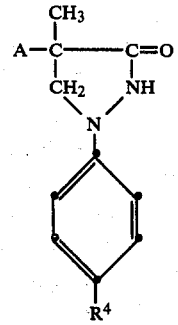

| ETA in Pod | A | R⁴ | $\lambda_{max}$ (nm) | Stain Density |
|---|---|---|---|---|
| Control 1 | —CH₃ | —CH₃ | 527 | 0.08 |
| Control 2 | —CH₂OH | —CH₃ | 527 | 0.22 |
| Compound 1 | —(CH₂)₂OH | —CH₃ | 527 | 0.15 |
| Compound 2 | —(CH₂)₃OH | —CH₃ | 529 | 0.18 |
| Compound 3 | —CH₂—CH(OH)CH₃ | —CH₃ | 526 | 0.19* 0.15* |
| Compound 4 | —CH₂—CH(OH)C₂H₅ | —CH₃ | 526 | 0.08* 0.15* |
| Control 3 | —CH₃ | —H | 517 | 0.04 |
| Control 4 | —CH₂OH | —H | 516 | 0.11 |
| Compound 5 | —(CH₂)₂OH | —H | 517 | 0.05 |

*Diastereoisomer pairs of compounds 3 and 4, isolated by thin-layer chromatography.

The above results indicate that while both Control 1 and Control 3 had low stain, Control 1 (as shown in Example 1) and Control 3 (in an independent test) gave substantial nitrogen evolution. Control 2 and Control 4, on the other hand, had higher stain. Compounds 1–5, according to the invention, had only moderate stain and evolved little nitrogen. In every case, less stain was obtained with the compounds according to the invention as compared to the corresponding 4-hydroxymethyl derivatives.

EXAMPLE 3

Synthesis of Compound 2: 4-(3-hydroxypropyl)-4-methyl-1-p-totyl-3-pyrazolidinone A. Bromo-1-(t-butyldimethylsiloxy)propane To a stirred solution at 0° C. under nitrogen of 3-bromopropanol (41.7 g, 0.3 mole) and t-butyldimethylsilyl chloride (49.7 g, 0.33 mole) in 300 ml dichloromethane was added sequentially triethylamine (37.0 g, 0.36 mole) and 4-(N,N-dimethylamino)pyridine (1.8 g, 0.015 mole). The mixture was stirred for one hour, allowed to warm to room temperature and filtered to remove salts. The salts were washed well with anhydrous ether; the combined filtrate was washed three times each with 75 ml ice-cold 10% aqueous hydrochloric acid, once with saturated aqueous sodium chloride, and dried over anhydrous magnesium sulfate. After removal of solvent, the residue was distilled to yield 46.0 g (61% yield) (BP 92°–93° C., 5mm).

B. 4-Methyl-1-p-tolyl-3-(t-butyldimethylsiloxy)-2-pyrazoline

To a stirred solution under nitrogen of 4-methyl-1-p-tolyl-3-pyrazolidinone (19.0 g, 0.10 mole) and t-butyldimethylsilyl chloride (16.6 g, 0.11 mole) in 200 ml toluene, was added sequentially triethylamine (10.6 g, 0.11 mole), 1,8-diazabicyclo- [5.4.0]-undec-7-ene (0.1 g), and 4-(N,N-dimethylamino) pyridine (0.1 g). The mixture was refluxed for 16 hours, cooled to room temperature and filtered. The salts were washed with ether and the solvents of the combined filtrate were removed under reduced pressure. The resulting residue was treated with 200 ml adhydrous ether, filtered to remove salts, and dried over anhydrous magnesium sulfate. Removal of the solvent yielded 29.8 g (98% yield).

C. 4-(3-Hydroxypropyl)-4-methyl-1-p-tolyl-3-pyrazolidinone

A solution of 4-methyl-1-p-tolyl-3-(t-butyldimethylsiloxy)- 2-pyrazoline (9.1 g, 0.030 mole) in 100 ml anhydrous tetrahydrofuran was added dropwise over a 20 minute period to a stirred solution under nitrogen at −78° C. of lithium diisopropylamide in 50 ml anhydrous tetrahydrofuran (note: the lithium diisopropylamide was generated at 0° C. by mixing 4.2 g diisopropylamine and 2.6 g n-butyllithium in 16.5 ml of n-hexane and 50 ml anhydrous tetrahydrofuran). The resulting orange-red solution was allowed to stir for 40 minutes at −78° C. and was then treated with a single portion of 3-bromo-1-(t-butyldimethylsiloxy)- propane (7.7 g, 0.031 mole) in 20 ml anhydrous tetrahydrofuran. After stirring for 16 hours and gradually being allowed to warm to room temperature, the mixture was diluted with 300 ml ether, and washed with 100 ml (1:1) saturated aqueous ammonium chloride/sodium chloride. The separated aqueous layer was dried over anhydrous magnesium sulfate and freed of solvent. A yield of 4.7 g (99%) was obtained.

The oil obtained above was digested in 250 ml anhydrous ether and washed vigorously with 100 ml 10% aqueous hydrochloric acid. The separated aqueous layer was extracted with 100 ml ether, and the combined organic phases were dried over anhydrous magnesium sulfate. Removal of the solvent yielded an oil which solidified upon standing. Evacuation to 0.1 mm pressure yielded 9.0 g (83% yield) of a waxy solid.

A stirred solution under nitrogen of the waxy solid obtained above (5.5 g, 0.015 mole) in 100 ml tetrahydrofuran was treated sequentially with 20 ml water and 1 ml trifluoroacetic acid. The mixture was stirred at room temperature for 2 hours, then diluted with 200 ml ether and washed with 50 ml portions each of water, saturated aqueous sodium bicarbonate and saturated aqueous sodium chloride. The organic layer was dried over anhydrous magnesium sulfate. After removal of the solvent under reduced pressure, the residue was digested in 100 ml hot ether, slowly cooled to 0° C., and allowed to crystallize for 3 hours. The solid recovered by filtration was 2.75 g (73% yield). Analysis was confirmed by infrared, $^1$HNMR, and $^{13}$CNMR spectra.

The above synthesis example has been provided for illustration only and is claimed in Michno U.S. application Ser. No. 520,085, filed of even date herewith, referred to above.

While specific utility for the compounds of this invention has been described for image transfer systems, these compounds would also be useful as developing agents in conventional black-and-white and color systems as well.

The invention has been described in detail with particular reference to preferred embodiments thereof, but it will be understood that variations and modifications can be effected within the spirit and scope of the invention.

What is claimed is:

1. An alkaline processing composition comprising a silver halide electron transfer agent having the following formula:

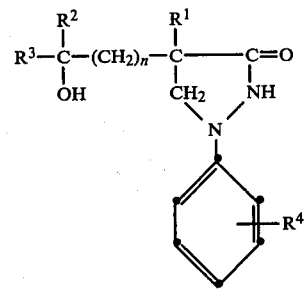

wherein:
n is 1 or 2;
$R^1$ represents an alkyl group of 1 to about 6 carbon atoms, an aryl or substituted aryl group of 6 to about 10 carbon atoms, or an aralkyl group of 6 to about 10 carbon atoms;
$R^2$ and $R^3$ each independently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms; and
$R^4$ represents hydrogen or one or more alkyl or alkoxy groups having from 1 to about 4 carbon atoms, methylenedioxy groups or ethylenedioxy groups.

2. The composition of claim 1 wherein $R^1$ is methyl and $R^2$ and $R^3$ are hydrogen.

3. The composition of claim 1 wherein $R^1$ is methyl, $R^2$ is hydrogen, n is 1 and $R^3$ is methyl or ethyl.

4. The composition of claim 1 wherein $R^4$ is methyl or methoxy located in the para-position.

5. A silver halide electron transfer agent compound or precursor thereof having the following formula:

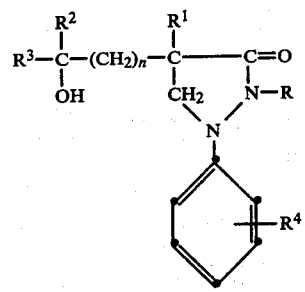

wherein:
n is 1 or 2;
R represents hydrogen or a hydrolyzable moiety;
$R^1$ represents an alkyl group of 1 to about 6 carbon atoms, an aryl or substituted aryl group of 6 to about 10 carbon atoms, or an aralkyl group of 6 to about 10 carbon atoms;
$R^2$ and $R^3$ each independently represents hydrogen, an alkyl or substituted alkyl group of 1 to about 6 carbon atoms, an aryl or substituted aryl group of 6 to about 10 carbon atoms, or an aralkyl group of 6 to about 10 carbon atoms; and $R^4$ represents hydrogen or one or more alkyl or alkoxy groups having from 1 to about 4 carbon atoms, methylenedioxy groups or ethylenedioxy groups.

6. The compound of claim 5 wherein R is hydrogen.

7. The compound of claim 6 wherein $R^1$ is methyl and $R^2$ and $R^3$ are hydrogen.

8. The compound of claim 6 wherein $R^1$ is methyl, $R^2$ is hydrogen, n is 1 and $R^3$ is methyl or ethyl.

9. The compound of claim 6 wherein $R^4$ is either methyl or methoxy located in the para-position.

* * * * *